(12) United States Patent
Carney et al.

(10) Patent No.: US 7,244,394 B2
(45) Date of Patent: Jul. 17, 2007

(54) METHODS AND KITS FOR ASSAYS OF ANALYTES OF INTEREST IN TEARS

(75) Inventors: Fiona Patricia Carney, Atlanta, GA (US); Jennifer Dawn Lane, Stone Mountain, GA (US); Carol Ann Morris, Duluth, GA (US)

(73) Assignee: Novartis AG, Basel (CH)

( * ) Notice: Subject to any disclaimer, the term of this patent is extended or adjusted under 35 U.S.C. 154(b) by 413 days.

(21) Appl. No.: 10/654,196

(22) Filed: Sep. 3, 2003

(65) Prior Publication Data

US 2004/0076547 A1 Apr. 22, 2004

Related U.S. Application Data

(60) Provisional application No. 60/415,914, filed on Oct. 3, 2002.

(51) Int. Cl.
| G01N 21/00 | (2006.01) |
| G01N 31/22 | (2006.01) |
| C08F 16/06 | (2006.01) |
| C08F 116/06 | (2006.01) |
| C08F 216/06 | (2006.01) |
| A61M 35/00 | (2006.01) |

(52) U.S. Cl. .................. 422/58; 422/56; 422/57; 521/141; 604/294

(58) Field of Classification Search ............ 422/56–58; 521/141; 604/294
See application file for complete search history.

(56) References Cited

U.S. PATENT DOCUMENTS

| 3,900,378 A | 8/1975 | Yen et al. ............... 204/159 |
| 4,540,408 A * | 9/1985 | Lloyd ...................... 604/294 |
| 4,635,488 A * | 1/1987 | Kremer .................. 73/864.72 |
| 4,951,683 A | 8/1990 | Davis ..................... 128/734 |

(Continued)

FOREIGN PATENT DOCUMENTS

| EP | 0 567 704 | 2/1997 |
| WO | WO 02/09589 | 2/2002 |

OTHER PUBLICATIONS

International Search Report.
European Search Report.
McCollum, Foulks, Bodner, Shepard, Daniels, Gross, Kelly and Cavanagh, "Rapid Assay of Lactoferrin in Keratoconjunctivitis Sicca", 1993, pp. 505-508.
Lemp, "Report of the National Eye Institue / Industry Workshop on Clinical Trials in Dry Eyes", 1995, pp. 221-232.
Xu, Yagi, Toda, Tsubota, "Tear Function Index", 1995, pp. 84-88.
Gachon, Richard and Dastugue, "Human tears: Normal Protein Pattern and Individual Protein Determinations in Adults", 1982, pp. 301-308.

(Continued)

*Primary Examiner*—Jill Warden
*Assistant Examiner*—Lore Ramillano
(74) *Attorney, Agent, or Firm*—Sheng-Hsin Hu; Jian Zhou (57) ABSTRACT

The invention, in one aspect, provides a strip for tear collection. The strip has a first end and an opposite second end and preferably has substantially uniform cross-sections from the first end to the second end. The strip is made of a hydrogel material in substantially dry state. The strip is characterized by having a substantially uniform swelling along the hydrogel strip from the first end to the second end when fully wicked by a tear fluid and by having a correlation between the volume of tear uptake by said strip and the length of the wicked end portion of said strip. A strip of the invention is useful for assay of an analyte of interest in a tear fluid. The invention also provides a method and kits for assaying an analyte of interest (e.g., lactoferrin, glucose, herpes simplex virus, hormones, etc.).

14 Claims, 2 Drawing Sheets

U.S. PATENT DOCUMENTS

| | | | | |
|---|---|---|---|---|
| 5,006,310 A | * | 4/1991 | Gin et al. | 422/56 |
| 5,170,799 A | | 12/1992 | Nagase et al. | 128/745 |
| 5,423,736 A | | 6/1995 | Cartmell et al. | 602/42 |
| 5,429,589 A | | 7/1995 | Cartmell et al. | 602/42 |
| 5,478,308 A | | 12/1995 | Cartmell et al. | 602/57 |
| 5,695,456 A | | 12/1997 | Cartmell et al. | 602/43 |
| 5,762,620 A | | 6/1998 | Cartmell et al. | 602/42 |
| 5,869,231 A | | 2/1999 | Romisch et al. | 435/4 |
| 5,884,630 A | | 3/1999 | Fujishima | 128/898 |
| 5,895,812 A | | 4/1999 | Laurie et al. | 530/388.2 |
| 5,899,871 A | | 5/1999 | Cartmell et al. | 602/43 |
| 6,087,185 A | * | 7/2000 | Lee-Own et al. | 436/514 |
| 6,219,574 B1 | | 4/2001 | Cormier et al. | 604/20 |
| 6,221,678 B1 | | 4/2001 | Chandler | 436/530 |
| 6,413,473 B1 | | 7/2002 | Bacon | 422/56 |
| 6,420,128 B1 | | 7/2002 | Ouyang et al. | 435/14 |
| 6,444,169 B1 | | 9/2002 | Evtodienko et al. | 422/56 |
| 6,444,435 B1 | | 9/2002 | Christner et al. | 435/14 |
| 6,448,067 B1 | | 9/2002 | Tajnafoi | 435/288.7 |
| 6,855,743 B1 | * | 2/2005 | Gvozdic | 521/141 |
| 2002/0013539 A1 | | 1/2002 | Hung | 600/573 |
| 2002/0098512 A1 | | 7/2002 | Goodell et al. | 435/7.1 |
| 2002/0106711 A1 | | 8/2002 | Tuohy et al. | 435/14 |
| 2002/0114735 A1 | | 8/2002 | Markart | 422/68.1 |
| 2002/0117639 A1 | | 8/2002 | Paolini et al. | 250/559.1 |

OTHER PUBLICATIONS

Klaeger, Cevallos, Sherman, Whitcher, and Stephens, "Clinical Application of a Homogenous Colorimetric Assay for Tear Lysozome", 1999.

PubMed, National Library of Medicine, Lactoferrin and "Dry Eye".

Jensen, Gluud, and Birgens, "The Concentration of Lactoferrin in tears during Post-Operative Ocular Inflammation" 1985, pp. 341-345.

* cited by examiner

METHODS AND KITS FOR ASSAYS OF ANALYTES OF INTEREST IN TEARS

This application claims the benefit under USC §119 (e) of U.S. provisional application No. 60/415,914 filed Oct. 3, 2002, incorporated by reference in its entirety.

The invention is related to a tear-collecting device, methods and kits for assays of analytes of interest in tears.

BACKGROUND OF THE INVENTION

Keratoconjunctivitis sicca (KCS) or "dry eye" is an ophthalmic condition defined by an insufficiency or imbalance of one or more of the ocular fluid components of an eye. Such imbalance may involve aqueous tear fluid, conjunctival mucin, and/or tear fluid lipid. KCS frequently threatens ocular anatomic integrity, often causing conjunctival and corneal erosion. "Dry eye" is a finding in about 25% of Sjogren's syndrome, which most often occurs in women past the age of 45 years. Sjogren's syndrome often detrimentally affects the immune system of the body; thus early detection and treatment is important. It has been estimated that several million persons in the United States alone are affected by KCS. 90% of such KCS cases are due to Sjogren's syndrome. KCS also commonly afflicts several canine species.

One of current diagnosis method for KCS is based on assay of lactoferrin. Lactoferrin, along with lysozyme, tear-specific prealbumin and lipocalin, is one of the major tear proteins synthesized and secreted by the lacrimal gland. It has been reported in the literature that lactoferrin is present in the acinar epithlial cells of both main and accessory lacrimal tissue by immunofluorescence histochemistry (Gillette, et al., Am. J. Ophthalmol 90: 30-37 (1980)). It is also reported that lactoferrin, lysozyme and tear-specific prealbumin are all decreased in the tear of patients with KCS (Jannsen and van Bijsterveld, Clin. Chim. Acta 114:207-208 (1981)). It is generally believed that if the lactoferrin concentration is equal or smaller than 0.9 mg/ml, it is classified as tear-deficiency dry eye.

Currently, there are two tests to assesses the lacrimal gland function by the amount of lactoferrin it produces in the tear film. One is the Lactoplate test, which is an immunodiffusion assay performed in an agarose gel containing rabbit antibody to human lactoferrin. Circular discs of filter paper are placed in the inferior conjuctiva cul-de-sac where they become "soaked" with tears. They are placed on the agar and incubated for three days. While it is accurate in moderate to severe dry eye states, this method is too cumbersome, slow, relatively expensive, and is limited by the experience of the examiner.

Another lactoferrin test is the LactoCard test, which is a solid phase ELISA test requiring only 2 μl of tears. The test is performed by a traumatic application of a 2-μl capilary tube to the lateral inferior tear meniscus to collect tear sample and the lactoferrin concentration in the tear sample is calorimetrically measured by a precise reflectance spectrometer. This test is suitable for office use and has been shown to be as accurate as the Lactoplate in determining tear lactoferrin level. Although the LactoCard test is easily performed in a clinician's office with minimal training, the tear collection by a capillary tube may be invasive or irritating. There is a need for an alternative tear collection device which can be a safer, much faster, and less irritating tear-collecting device.

SUMMARY OF THE INVENTION

One object of the invention is to provide a new tear collection device which is less-invasive and user-friendly.

Another object of the invention is to provide a method and kits for assaying lactoferrin level in a tear fluid. Such method and kits have relatively high sensitivity and reliability and are suitable for patients to carry out the lactoferrin assays in a more convenient and discreet manner (e.g., at an optometrist's office or at home).

A still another object of the invention is to provide a method and kits for assaying an analyte of interest (e.g., lactoferrin, glucose, herpes simplex virus, hormones, etc.).

These and other objects of the invention are met by the various aspects of the invention described herein.

The invention, in one aspect, provides a strip for tear collection. The strip has a first end and an opposite second end and preferably has substantially uniform cross-sections from the first end to the second end. The strip is made of a hydrogel material in a substantially dry state. The strip is characterized by having a substantially uniform swelling along the hydrogel strip from the first end to the second end when fully wicked by a tear fluid and by having a correlation between the volume of tear uptake by said strip and the length of the wicked end portion of said strip.

The invention, in another aspect, provides a method for assaying an analyte of interest in a tear fluid of an eye. The method comprises: placing an end portion of a strip at a location in the eye away from the cornea of the eye to wick (absorb) an amount of the tear fluid, wherein said strip is made of a hydrogel material in a substantially dry state and preferably has substantially uniform cross-sections from one end to the other end, wherein said strip is characterized by having a substantially uniform swelling along the hydrogel strip from one end to the other end when fully wicked by the tear fluid and by having a defined correlation between the volume of tear uptake by said strip and the length of the tear-wicked end portion of said strip; separating a fraction or all of the tear-wicked end portion of said strip from the rest portion; determining the presence or the amount of the analyte of interest using the fraction or all of the tear-wicked end portion of said strip.

The invention, in still another aspect, provides a kit for assaying an analyte of interest in a tear fluid of an eye. The kit comprises: a strip for collecting the tear fluid, wherein said strip has a first end and an opposite second end and preferably has substantially uniform cross-sections from the first end to the second end, wherein said strip is made of a hydrogel material in a substantially dry state and is characterized by having a substantially uniform swelling along the hydrogel strip from the first end to the second end when fully wicked by a tear fluid and by having a correlation between the volume of tear uptake by said strip and the length of a tear-wicked end portion of said strip; and a testing agent composition which specifically reacts or interacts with the analyte of interest to form a detectable signal.

DETAILED DESCRIPTION OF PREFERRED EMBODIMENTS

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

The invention, in one aspect, provides a strip for tear collection. The strip is made of a hydrogel material in a substantially dry state and preferably has a uniform cross-section. A hydrogel strip of the invention is characterized by having a substantially uniform swelling along the hydrogel strip when fully wicked by a tear fluid and characterized by having a correlation between the volume of tear uptake by said strip and the length of the tear-wicked end portion of said strip.

It has been discovered that a hydrogel material is well suitable for making a tear-collecting strip (or wick). It has been found here that: (1) the length of the wicked portion of a poly(vinyl alcohol) (i.e. PVA) strip correlates well with the volume of uptake by the PVA strip; (2) analytes (e.g., glucose) of interest in a tear fluid can be absorbed by a PVA strip and distributed over the entire tear-wicked portion of the PVA strip in a well defined fashion laterally along the PVA strip; (3) a tear fluid and/or analytes of interest can be substantially recovered from a tear-wicked PVA strip. With such features, a hydrogel strip can work well as an alternative form of tear collection device to replace glass capillary tubes.

A hydrogel strip as a tear-collecting device can offer some advantages over a glass capillary tube. First, it is much easier to handle a hydrogel strip than to handle a glass capillary tube. A glass capillary tube may break and potentially cause injury during handling and transportation. Liquid contained in a glass capillary tube can be spilled (or dropped) out by accident to cause some health or environmental concerns. In contrast, a hydrogel strip is not fragile. Once a tear fluid is absorbed, it is confined by the hydrogel strip so that problems associated with spilling out of liquid is eliminated or at least minimized. Second, it is safer, much faster, and less irritating to use a hydrogel strip than to use a glass capillary tube in collecting tear fluids. Capillary tubes are generally hard and relatively sharp because of their small cross-section dimension and their thin walls. However, hydrogels are soft, especially when hydrated (i.e., after absorbing a tear fluid) and have been widely used in contact lenses. Compared with a glass capillary tube, a hydrogel strip is less likely to cause damage to an eye and can be used by a person who is not a well trained professional. Furthermore, assays for one or more analytes of interest can be carried out directly on and in one or more divided pieces of the tear-wicked portion of a hydrogel strip. Or, a tear fluid absorbed by a hydrogel strip can be substantially recovered by a method known to a person skilled in the art.

A "hydrogel material" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "monomer" means a low molecular weight compound that can be polymerized. Low molecular weight typically means average molecular weights less than 700 Daltons.

A "macromer" refers to a medium and high molecular weight compound or polymer that contains functional groups capable of further polymerization. Medium and high molecular weight typically means average molecular weights greater than 700 Daltons.

A "hydrophilic vinylic monomer" refers to a monomer which as a homopolymer typically yields a polymer that is water-soluble or can absorb at least 10 percent by weight water. Suitable hydrophilic vinylic comonomers include, without limitation, hydroxy-substituted lower alkylacrylates and -methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkylvinyl-ethers, sodium ethylene sulphonate, sodium styrene sulphonate, 2-acrylamido-2-methyl-propane-sulphonic acid, N-vinyl pyrrole, N-vinyl succinimide, N-vinyl pyrrolidone, 2- or 4-vinyl pyridine, acrylic acid, methacrylic acid, amino- (whereby the term "amino" also includes quaternary ammonium), mono-lower-alkylamino- or di-lower-alkylamino-lower-alkyl-acrylates and -methacrylates, allyl alcohol and the like. Preference is given e.g. to hydroxy-substituted $C_2$-$C_4$-alkyl(meth)acrylates, five- to seven-membered N-vinyl-lactams, N,N-di-$C_1$-$C_4$-alkyl-methacrylamides and vinylically unsaturated carboxylic acids with a total of 3 to 5 carbon atoms. Examples of suitable hydrophilic vinylic comonomers include hydroxyethyl methacrylate, hydroxyethyl acrylate, acrylamide, methacrylamide, dimethylacrylamide, allyl alcohol, vinyl pyridine, vinyl pyrrolidone, glycerol methacrylate, N-(1,1-dimethyl-3-oxobutyl)acrylamide, and the like.

Any known, suitable hydrogels can be used in the invention. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, silicone-containing hydrogels, polyurethane, polyurea, and the like. A hydrogel can be prepared according to any methods known to a person skilled in the art.

Preferably, a strip is placed at a location near the lateral canthus of an eye to collect tear fluids. "Lateral canthus" refers to one of the two canthuses of an eye, which is located away from the nose.

A hydrogel strip of the invention can have any dimension suitable for collecting tear fluids. A hydrogel strip of the invention has a length sufficient long to absorb a minimum volume of tear (e.g., at least about 1 µl). A hydrogel strip of the invention is preferably at least 15 mm in length, more preferably at least 30 mm in length.

It is not desirable that the cross-section of a hydrogel strip has a dimension (e.g, diameter, width, height, etc.) too small so that the hydrogel strip become sharp and can cause damages to eye tissues, and/or the hydrogel strip becomes not structurally steady.

It is also not desirable that the cross-section of a hydrogel strip has a dimension (e.g, diameter, width, height, etc.) too large so that the hydrogel strip can not access the lateral canthus.

A hydrogel strip of the invention preferably has a uniform cross-section along the strip. The cross-section of a hydrogel strip of the invention can have any geometric shape, for example, such as rectangular, square, circular, triangular, annular ring, or the like. Preferably, the cross-section of a hydrogel strip has a rectangular shape. The rectangular cross-section has a width of from about 1 mm to about 3 mm, preferably from 1.5 mm to 2 mm, and a height of from 0.5 mm to 1.5 mm, preferably from 0.8 mm to 1.2 mm. Where the cross-section of a hydrogel strip of the invention is circular, the diameter of the circular cross-section is preferably from 1 mm to 3 mm, more preferably from 1.5 mm to 2.2 mm.

A "substantially uniform swelling along the hydrogel strip when fully wicked by a tear fluid" means that when a hydrogel strip of the invention is fully wicked by a fluid (e.g., a tear), it has a substantially uniform increase in volume along the length of the hydrogel strip and no significant change in the geometric shape of the strip can be observed.

Correlation between the volume of fluid (e.g., tear, serum, or urine) uptake by said strip and the length of the fluid-wicked end portion of said strip preferably is a substantially linear relationship. With a substantially linear correlation, the volume of tear uptake by a hydrogel strip of the invention can be easily quantified. In a preferred embodiment, the volume of tear uptake is noticeably marked on a hydrogel strip of the invention.

Figure 1:
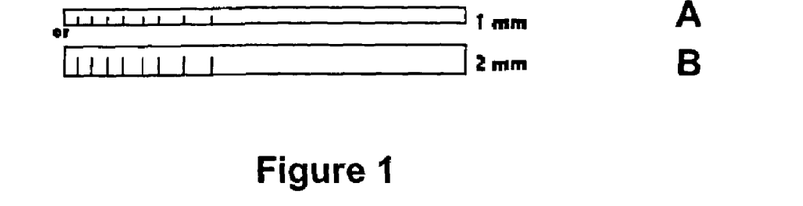
FIG. 1A is a schematic side view of a strip according to a preferred embodiment of the invention.
FIG. 1B is schematic top view of the strip shown in FIG. 1A.

For example, a hydrogel strip according to a preferred embodiment of the invention is schematically shown in FIG. 1. In this preferred embodiment, the cross-section of the hydrogel strip is rectangular and the hydrogel strip has a dimension of 1.5 mm in width, 1.0 mm in height, and 30 mm in length. Scales of tear uptake and serum uptake by the strip are marked respectively on the top and side of the strip.

The invention, in another aspect, provides a method for assaying an analyte of interest in a tear fluid of an eye. The method comprises: placing an end portion of a strip at a location in the eye away from the cornea of the eye to wick (absorb) an amount of the tear fluid, wherein said strip is made of a hydrogel material in substantially dry state and preferably has substantially uniform cross-sections from one end to the other end, wherein said strip is characterized by having a substantially uniform swelling along the hydrogel strip from one end to the other end when fully wicked by the tear fluid and by having a defined correlation between the volume of tear uptake by said strip and the length of the tear-wicked end portion of said strip; separating a fraction or all of the tear-wicked end portion of said strip from the rest portion; determining the presence or the amount of the analyte of interest using the fraction or all of the tear-wicked end portion of said strip.

The term "analyte" refers to a substance being tested. Exemplary analytes of interest include, but are not limited to, electrolytes and small molecules (e.g., sodium, potassium, chloride, phenylalanine, uric acid, galactose, glucose, cysteine, homocysteine, calcium, ethanol, acetylcholine and acetylcholine analogs, ornithine, blood urea nitrogen, creatinine), metallic elements (e.g., iron, copper, magnesium), polypeptide hormones (e.g., thyroid stimulating hormone, growth hormone, insulin, luteinizing hormones, chorionogonadotrophic hormone, obesity hormones such as leptin, serotonin and the like), chronically administered medications (e.g., dilantin, phenobarbital, propranolol), acutely administered medications (e.g., cocaine, heroin, ketamine), small molecule hormones (e.g., thyroid hormones, ACTH, estrogen, cortisol, estrogen, and other metabolic steroids), markers of inflammation and/or allergy (e.g., histamine, IgE, cytokines), lipids (e.g., cholesterol), proteins and enzymes (e.g., lactoferrin, lysozymes, tear-specific prealbumin, albumin, complement, coagulation factors, liver function enzymes, heart damage enzymes, ferritin), markers of infection (e.g., virus components, immunoglobulins such as IgM, IgG, etc., proteases, protease inhibitors), and/or metabolites (e.g., lactate, ketone bodies).

An analyte of interest can be assayed directly on a fraction or all of the tear-wicked portion of the strip or by first recovering the tear sample from the wicked portion of the strip and then assaying the one or more analytes of the interest in the recovered tear sample.

It is well known to a skilled artisan that assay of an analyte of interest can be carried out with the help of a testing agent composition which specifically reacts or interacts with the analyte of interest, leading to formation of a detectable signal. A detectable signal, for example, can be electrical signals (electrochemical assays), or optical signals (enzyme assays, immunoassays or competitive binding assays). Exemplary electrical signals are electrical potentials and currents. Optical signals refers to changes in the optical properties, including, but not limited to, a color formation, a change in color, fluorescence, luminescence, chemiluminescence, changes in fluorescence or luminescence intensity, changes in fluorescence or luminescence lifetimes, fluorescent anisotropy or polarization, a spectral shift of the emission spectrum, time-resolved anisotropy decay, and the like.

Electrochemical assay of an analyte of interest is largely carried out by using an enzymatic electrode (or biosensor) which consists of a thin layer of enzymes adsorbed to the active surface of a transducer. Along with a suitable reference electrode and a circuit, a biosensor allows to measure either the potential difference generated between the two electrodes (for potentiaometric measurements) or the current that flows between the two electrodes (for amperometric measurements). An example of biosensor is glucose biosensor, which consists of a carbon electrode with a conductive coating containing a mixture of glucose oxidase and mediator. At the working electrode surface glucose is oxidized by the glucose oxidase enzyme. This reaction causes the mediator to be reduced. At the fixed potential, applied between the two electrodes the mediators is oxidized, generating a signal response which correlates with the glucose concentration in a sample.

The hydrogel strip can be served as a medium for performing an electrochemical assay. For example, the electrochemical assay of an analyte of interest in a tear fluid can be carried out by first collecting an amount of the tear fluid using a hydrogel strip of the invention, then by placing the whole or fractional tear-wicked portion of a hydrogel strip in direct contact with an enzyme electrode and a reference electrode, and finally by applying a fixed potential between the two electrodes to obtain an amperometric signal (current) that correlates with the concentration of the analyte of interest.

Immunoassay has been widely used in the determination of an analyte of interest in a biological fluid, such as urine or serum. For example, lactoferrin can be assayed by a solid phase ELISA test similar to that for LactoCards test. In another example, glucose can be assayed based on the Trinder reaction. Typically in the Trinder reaction, glucose oxidase, in the presence of oxygen, oxidizes glucose to form gluconic acid and hydrogen peroxide which in turn reacts with a chromogenic oxidation/reduction indicator (e.g., phenol, 3-hydroxy-2,4,6-triiodobenzoic acid, 3-hydroxy-2,4,6-tribromobenzoic acid, etc.) in the presence of peroxidase to form a color different from its original color or to generate a chemiluminescence. The Trinder reaction can be used to determine other analytes of interest so long an analyte-specific oxidase can be obtained and used.

Binding assays and competitive binding assays have been widely used in the determination of an analyte of interest in a sample. Typically, a binding assay (without use of any competitor) is generally carried out by using a protein or fragment thereof or a chemical compound (as a receptor) that is capable of binding said analyte (ligand) in said sample and has a detectable optical signal (or other detectable signal) that changes in a concentration-dependent manner when the protein is bound to said analyte. A competitive binding assay is based on the competition between a labeled ligand (analyte) or ligand analogue (analyte-analogue) and an unlabeled ligand (analyte) in the reaction with a receptor (e.g., antibody, receptor, transport protein, chemical compound).

The detectable optical signal results from one or more labels associated with a receptor and/or a competitor. A label may be covalently or non-covalently bound to a receptor or a competitor. A "receptor" refers to a protein or fragment thereof or a chemical compound that is capable of binding reversibly an analyte of interest in a sample. A "competitor" refers to a molecule or moiety that competes with an analyte of interest for binding to a receptor.

A wide range of suitable labels are known. For example, the label may be a fluorescent label. "A fluorescent label" refers to a moiety that comprises at least one fluorophore and that, when attached to a molecule, render such molecule detectable using fluorescent detection means. Exemplary fluorophores include xanthene-type dyes, fluorescein-type dyes, rhodamine-type dyes, cyanine-type dyes, and the like. A fluorophore can also be a fluorescent protein such as phycobiliproteins.

The detectable optical signal can be derived from a pair of fluorophores, a first fluorophore and a second fluorophore. One of the two fluorophores can be an energy donor, for example the first fluorophore, which absorbs energy upon excitation at an excitation wavelength within its absorption spectrum and emits energy at a wavelength within its emission spectrum, and the other fluorophore can be an energy acceptor, for example the second fluorophore, which accepts the energy emitted by the donor at a wavelength within the absorption spectrum of the acceptor and emits energy at a wavelength within the emission spectrum of the acceptor. The wavelength of the absorption maximum of the donor fluorophore is shorter than the wavelength of the absorption maximum of the acceptor fluorophore; and the wavelength of the emission maximum of the donor fluorophore is shorter than the wavelength of the emission maximum of the acceptor fluorophore. It is known that the energy transfer efficiency depends on the several factors such as spectral overlap between the emission spectrum of the donor and the absorption spectrum of the acceptor, spatial distance between donor and acceptor fluorophores, relative orientation of donor and acceptor fluorophore, quantum yield of the donor and excited state lifetime of the donor. It is well known to a person skilled in the art how to select a donor fluorophore and a acceptor fluorophore. In a binding assay system, the energy donor fluorophore and the energy acceptor fluorophore each can be bound to a receptor and spaced such that there is a detectable optical signal when the receptor is bound to the analyte. In a competitive binding assay system, one of the energy donor fluorophore and the energy acceptor fluorophore can be bound to the receptor and the other can be bound to the competitor.

It is understood that the above energy acceptor fluorophore can be replaced by a non-fluorescent energy transfer acceptor, for example, such as a dye which accepts the energy emitted by the donor fluorophore at a wavelength within the absorption spectrum of the acceptor but does not emits energy in the form of fluorescence or luminescence.

A fluorescent label can intrinsically be part of the receptor. For example, a receptor can be a fusion protein comprising at least the fluorescent part of a fluorescent protein and at least the binding part of a receptor protein. Alternatively, the fluorescent label can be a fluorescent label which is not naturally associated with the receptor moiety but which is attached by means of a chemical linkage, such as a covalent bond.

A fluorescent label can intrinsically be part of the competitor. Alternatively, the fluorescent label can be a fluorescent label which is not naturally associated with the competitor moiety but which is attached by means of a chemical linkage, such as a covalent bond.

One example of binding assay is an assay for glucose disclosed in U.S. Pat. No. 6,197,534, using an *E. coli* glucose/galactose binding protein ("GGBP") as previously described (Scholle, et al., *Mol. Gen. Genet* 208:247-253 (1987)), or functionally equivalent fragments thereof. As a sensor for glucose monitoring, GGBP has several favorable features including a single glucose binding site and high affinity for glucose; GGBP binds glucose with a dissociation constant near 0.8 µM. Like similar transport proteins from other bacteria, GGBP is highly specific for binding glucose and/or galactose. The apparent binding affinity of GGBP for sugars other than glucose or galactose is typically 100-1000 fold weaker [Boos, et al., *J. Biol. Chem.* 247(3):917-924 (1972); Boos, W., *J. Biol. Chem.* 247(17):5414-5424 (1972); Strange and Koshland, *Proc. Nat'l Acad. Sci. USA* 73(3): 762-766 (1976); Zukin, et al., *Biochemistry* 16(3):381-386 (1977)). The high affinity for glucose also will allow to measure µM glucose concentrations in a tear fluid. GGBP can be labeled with one fluorescence energy donner moiety and one fluorescence energy acceptor at two specific position on GGBP in a manner so that there is a detectable spectral change (e.g., change in fluorescence intensity or lifetime) when GGBP is bound to glucose.

One example of a competitive binding assay is an assay for glucose disclosed in U.S. patent application Ser. No. 09/784,471, using a glucose-sensing system which comprises tetramethylrhodamine isothiocyanate concanavalin A (TRITC-ConA) as a receptor, fluorescein isothiocyanate dextran (FITC-dextran) as a competitor. While the FITC-dextran is bound to the TRITC-ConA, the FITC fluorescence is quenched by TRITC via a fluorescence resonance energy transfer. Increased glucose concentration frees the FITC-dextran and results in fluorescence which is proportional to glucose concentration.

The hydrogel strip can be served as a medium for performing a binding assay or a competitive binding assay using a testing agent composition which specifically reacts or interacts with the analyte of interest to form a detectable signal.

Where an analyte of interest in a tear fluid is assayed based on a binding assay, the testing agent composition preferably comprises a receptor that is capable of binding said analyte of interest and has a detectable optical signal that changes in a concentration-dependent manner when the protein or fragment thereof is bound to said analyte, wherein said detectable optical signal results from one or more labels associated with the receptor. More preferably, the testing agent composition comprises: (1) a fluorescence energy donor and a fluorescence energy acceptor; or (2) a fluorescence energy donor and a non-fluorescence energy acceptor.

Where an analyte of interest in a tear fluid is assayed based on a competitive binding assay, the testing agent composition preferably comprises a receptor having a first label associated therewith, a competitor having a second label associated therewith, wherein one of the first and second labels is a fluorescent energy donnor and the other one is a fluorescent or non-fluorescent energy acceptor. Binding of both the competitor and the analyte to the analyte/competitor binding site is reversible.

A testing agent composition can be a solution or can be incorporated partially or fully in a strip of the invention. For example, the receptor can be covalently bound to the strip material. The receptor can be covalently linked to the strip material according to any known, suitable methods.

Similarly, a competitor can be tethered, preferably via a flexible linker, to the strip material according to any known, suitable methods. Introduction of flexible linkers into a polymer or a competitor or receptor is known to a person skilled in the art.

Again, it is well within the skill of those in the art to select a competitor which will compete with an analyte for binding to a particular analyte/competitor binding site of a receptor. For example, competitor which can be used with the analyte-receptor. binding pairs disclosed above include fluorescein dextran (which competes with glucose for binding to concanavalin A), 2-deoxy-D-glucose or D-mannose or D-galactose (which competes with glucose for binding to glucose oxidase), fluorescein polyglutamylurate (which competes with uric acid for binding to uricase), fluorescein nanolol (which competes with alcohol for binding to alcohol dehydrogenase), fluorescein-glutamine phenylacetate (which competes with phenylalnine for binding to phenylalanine hydroxylase), fluorescein-erythrocuprein (which competes with copper for binding to ceruloplasmin), fluorescein-2,3,6-tri-O-methyl galactose (which competes with galactose for binding to galactokinase), fluorescein-S-adenosyl polyhomocysteine (which competes with cysteine and homocysteine for binding to cystathionine synthetase), fluoropolyglutamyl prostigmine (which competes with acetylcholine for binding to acetylcholinesterase), and fluorospermine (which competes with ornithine for binding to diamine oxidase).

The nature of the molecule used as the receptor depends on the particular analyte to be detected, but minimally includes that portion of the molecule which is sufficient to contain an analyte/competitor binding site. For example, if glucose is the analyte to be detected, the receptor preferably is Concanavalin A (Mansouri & Schultz, *Bio/Tech* 2, 385, 1984) or glucose oxidase (preferably an unreactive form), boronic acid, or a genetically engineered glucose binding protein, although other receptors, such as antibodies, also can be used.

If phenylalanine is the analyte to be detected, the receptor preferably comprises the active site of phenylalanine hydroxylase. It is well within the skill of those knowledgeable in the art to determine other analyte-receptor moiety binding pairs, such as uric acid-uricase, alcohol-alcohol dehydrogenase, copper-ceruloplasmin, galactose-galactokinase, cysteine- and/or homocysteine-cystathionine synthetase, acetylcholine-acetylcholinesterase, ornithine-diamine oxidase, and the like.

Preferably, a fluorescent label associated with a competitor in a testing agent composition for competitive binding assay is more readily detectable when the competitor is not bound to the analyte/competitor binding site. Thus, fluorescent labels, such as fluorescein, indocyanine green, malachite green, rhodamine, Alexa Fluor® dyes (e.g., Alexa 488), Oregon Green® dyes (e.g., Oregon Green 488), BODIPY (4,4-difluoro-4-bora-3a,4a-diaza-s-indacene) fluorophores, cyanine dyes (e.g., Cy2), and phycobiliproteins, which are quenched when the competitor is bound but are unquenched when the competitor is not bound, are preferred according to embodiments of the invention.

In another embodiment, a strip of the invention comprises, on its surface, a receptor layer, a polyelectrolyte layer, and a competitor layer. The polyelectrolyte layer includes one or more polyelectrolytes, which are generally high molecular weight polymers with multiple ionic or ionizable functional groups. At least one polyelectrolyte in the polyelectrolyte layer has a charge opposite to the overall charge of the receptor and competitor layers. Suitable polyelectrolytes include positively charged PDDA (polydiallyldimethylammonium chloride) and negatively charged PM (polyacrylic acid). Assembly of the layers is based upon sequential adsorption of oppositely charged polyions. The sensor and spacing polyelectrolytes are deposited as uniform thin films (1-10 nm) in 10-15 deposition cycles onto the porous polyvinyl alcohol or hydrogel matrix, resulting in only a 100-500 nm thick coating for the sensing film, which is highly biocompatible. A typical sequence for construction of a strip of the invention suitable for glucose detection involves a deposition cycle of ultrathin (1-10 nm) films of PDDA, PAA, PDDA, concanavalin A, PDDA, PAA, PDDA, fluorescein dextran, PDDA, PAA, PDDA, PAA, concanavalin A, PAA, fluorescein dextran, PAA, etc. Technology for constructing ophthalmic lenses comprising such layers is taught, for example, in WO 99/35520.

Labels can be detected by any method known to a person skilled in the art. For example, if the label is a luminescent label, the detector may include a luminometer; if the label is a colorimetric label, the detector may include a colorimeter; if the label is a fluorescent label, the detector may include a fluorophotometer. Construction of such devices is well known in the art. Light with wavelengths which will excite the fluorescent label can be provided, for example, by a laser or a light source, such as a light-emitting diode.

The invention, in still another aspect, provides a kit for assaying an anaylte of interest in a tear fluid, the kit comprising: a strip for collecting the tear fluid, wherein said strip has a first end and an opposite second end and preferably has substantially uniform cross-sections from the first end to the second end, wherein said strip is made of a hydrogel material in substantially dry state and is characterized by having a substantially uniform swelling along the hydrogel strip from the first end to the second end when fully wicked by a tear fluid and by having a correlation between the volume of tear uptake by said strip and the length of a tear-wicked end portion of said strip; and a testing agent composition which specifically reacts with the analyte of interest to form a detectable signal.

Methods and kits of the invention are useful for diagnostic purposes, for example to diagnose dry eye (to determine lactoferrin concentration in a tear fluid of a patient), to monitor glucose level, to test for pregnancy (to detect β-HCG), to assess blood chemistry (electrolytes, $Ca_2PO_4$, magnesium, bilirubin, alkaline phosphatase, lactate dehydrogenase, alanine aminotransferase, etc.), and to detect infection (e.g., by detecting components of viruses such as CMV, EBV, hepatitis, and HIV, or bacteria, such as Staphlococcus, Streptococcus, etc.). They also are useful for monitoring blood levels of test compounds during the course of assessing the compounds for use as potential therapeutics.

Dry eye patients could be diagnosed at home or in an optometrist's office by collecting a tear sample with a hydrogel strip of the invention. The strip could either contain a testing agent composition to perform a calorimetric assay directly on it, or, the strip could be placed directly into an assay system for determining lactoferrin concentration in a tear fluid. This would allow optometrists to diagnose dry eye in each patient visit.

At least one component or all components of a testing agent composition can be optionally impregnated in a strip of the invention for assaying an analyte of interest in a tear fluid.

The previous disclosure will enable one having ordinary skill in the art to practice the invention. In order to better enable the reader to understand specific embodiments and the advantages thereof, reference to the following examples is suggested.

EXAMPLE 1

Figure 3:
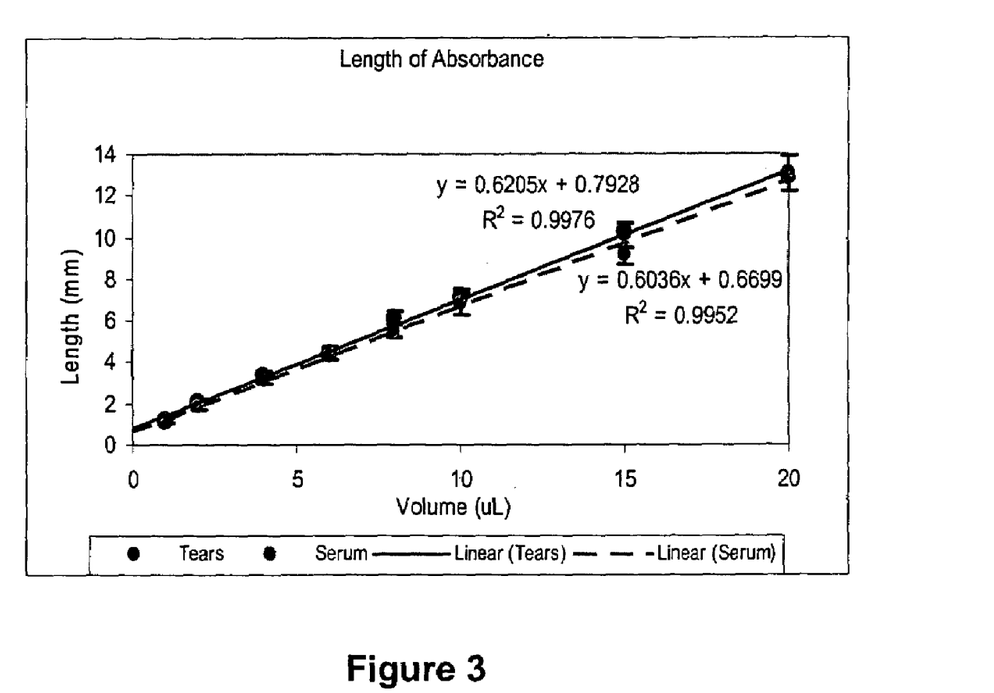
FIG. 3 shows the relationship between the length of an end portion, wicked by a fluid sample, of a strip of the invention and the sample uptake by said strip.

Poly(vinyl alcohol) (PVA) material is supplied by Ultracell. Wicks (strips) are prepared to have a dimension of 1.5 mm in width, 1.0 mm in depth and 30 mm in length as shown in FIG. 1. One of the two ends of a wick is dipped in a known volume of sample, such as tear, serum or phosphate buffer (PBS) (ca. pH 7.2). When a sample is absorbed (wicked) by the wick, the uptake on the wick is clearly visible. The length of the wicked portion of the wick for a given volume of sample is measured. This experiment is repeated 20 times. Reproducible linear curves are obtained, as shown in FIG. 3. The linear relationship between the length of the wicked portion of a PVA wick and the volume of uptake on the PVA wick is L (μl)=0.6205·Vol+0.7928 and L (μl)=0.6036·Vol+ 0.6699 respectively for tear and serum. The $R^2$ values for tears and serum both are 0.99. The reproducibility of volume uptake is not as easily observed in three other design iterations including three cylindrical PVA wicks of varying diameter (2.25 mm, 1.75 mm, and 2.15 mm) and identical length (28 mm).

Based on the above-established linear relationship between the length of the wicked portion and the volume of uptake, a scale can be established as shown in Table 1. Such scale can be marked or stamped on the side or top of the wick, denoting the volume of tears or serum collected. A separate scale is required for tears and serum. Preferably, the scale for tears can be marked on the top of the wick and the scale for serum on the side of the wick, or vice versa.

TABLE 1

| Volume (μL) | Tears Length (mm) | Serum Length (mm) |
| --- | --- | --- |
| 1 | 1.164 | 1.229 |
| 2 | 2.056 | 1.890 |
| 4 | 3.288 | 3.141 |
| 6 | 4.421 | 4.400 |
| 8 | 6.088 | 5.504 |
| 10 | 7.062 | 6.826 |
| 15 | 10.268 | 9.112 |
| 20 | 12.950 | 13.100 |

EXAMPLE 2

Figure 2:
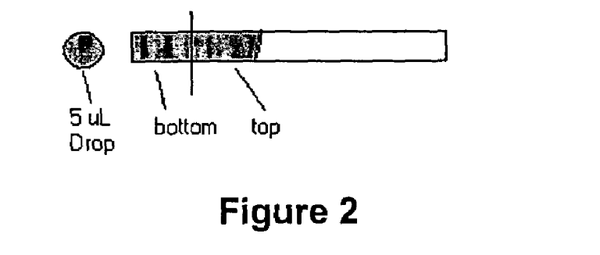
FIG. 2 schematically depicts the wicked end portion of a strip according to a preferred embodiment of the invention.

PVA wicks are prepared as described in Example 1. Three glucose solutions are prepared by dissolving glucose respectively in three media, PBS, tear and serum. The concentration of glucose is 150 mg per 100 ml. A wick is dipped in 5 μl of a glucose solution. After all of the solution is absorbed (wicked) by the wick, the wicked portion of the wick is cut in half. Each half (Shown in FIG. 2) is then assayed for glucose using the commercially available Trinder assay from Sigma.

Figure 4:
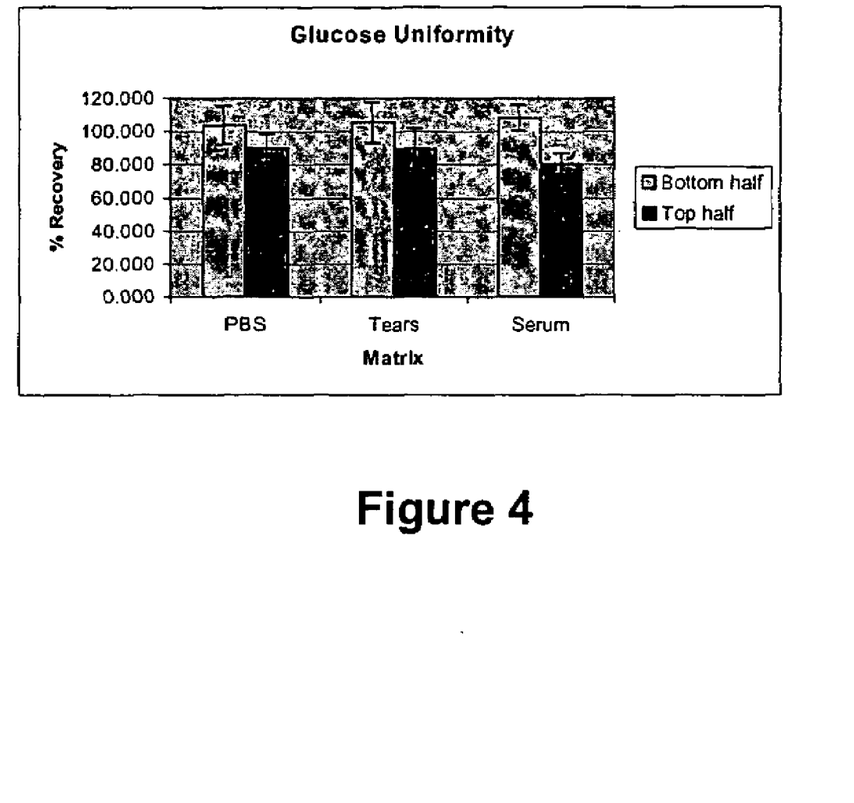
FIG. 4 shows the distributions of glucose in the bottom and top halves of the wicked end portion of a strip of the invention.

Results are shown in FIG. 4. Glucose in each of the three solutions is taken up by wicks. However, there is difference in the glucose uptake between the bottom half (i.e., containing the dipping end of the wick) and the top half. Such difference depends on the presence of other chemicals, for example, such as proteins, in a medium for preparing a glucose solution under study. The biggest difference is observed in the case where serum is used in preparation of glucose solution. However, it appears that the difference in glucose uptake between the bottom and top halves is consistent for a given medium for preparing glucose solution. Therefore, it is possible to establish an algorithm to define approximately the uptake of glucose along a wick for a given sample (tear or serum).

EXAMPLE 3

Tear samples have been collected from subjects using PVA wicks and glass capillary tubes in order to be assayed for total protein. It has been discovered that tear collection is much easier and faster using wicks. More tear fluid can be collected by means of PVA wicks in a shorter period of time compared to glass capillary tubes.

EXAMPLE 4

Figure 5:
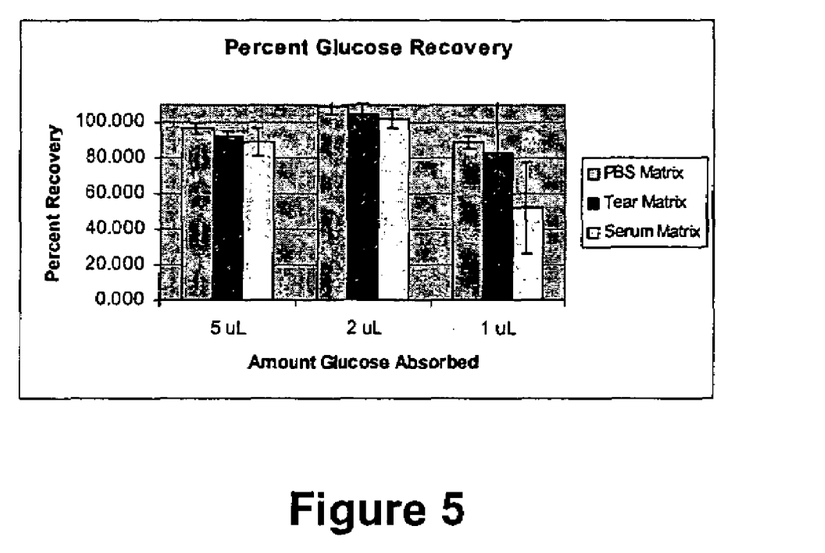
FIG. 5 shows the percentage of glucose recovery from the wicked portion of a strip of the invention.

PVA wicks are dipped in various volumes of a known concentration of glucose solution. This solution is either prepared from a medium, such as PBS, serum or tears. The entire portion of a wick containing uptake is then assayed for glucose using the Trinder assay and the percent recovery under each condition is determined (FIG. 5). Recovery is within a range of 90% for most experiments except the case of 1 μl of glucose-containing serum. The greater the volume taken up the higher the recovery. The result of the experiment with 1 μl of glucose-containing serum may probably due to human errors, which is the same for the glass capillary tubes. Recovery of the glucose concentration was also observed using a dilution method followed by lyophilization of the collected volume. Using this lyophilization method and dissolving the recovered lyophile in a known volume (i.e. 10 μL), greater than 80% recovery was observed at various glucose concentrations. Overall, this series of experiments confirm that wicks can be used to replace glass capillary tubes.

What is claimed is:

1. A kit for assaying an analyte of interest in a tear fluid of an eye, comprising: a strip for collecting the tear fluid, wherein said strip has a first end and an opposite second end, wherein said strip is made of a hydrogel material in substantially dry state and is characterized by having a substantially uniform swelling along the hydrogel strip from the first end to the second end when fully wicked by a tear fluid and by having a correlation between the volume of tear uptake by said strip and the length of a tear-wicked end portion of said strip, wherein said hydrogel material is obtained by polymerization or copolymerization of at least one hydrophilic monomer in the presence of or in the absence of additional monomers and/or macromers and is selected from the group consisting of poly(vinyl alcohol), modified polyvinylalcohol, poly(hydroxyethyl methacrylate), poly(vinyl pyrrolidone), poly(vinyl alcohol) with polycarboxylic acids, polyacrylamide, polymethacrylamide, silicone-containing hydrogels, polyurethane, polyurea, and mixtures thereof; and a testing agent composition which specifically reacts with the analyte of interest to form a detectable signal.

2. A kit of claim 1, wherein the cross-section of said strip is circular, and wherein the diameter of the circular cross-section is from 1 mm to 3 mm.

3. A kit of claim 1, wherein the cross-section of said strip is rectangular and has a width of from about 1 mm to about 3 mm and a height of from 0.5 mm to 1.5 mm.

4. A kit of claim 1, wherein said defined correlation between the volume of tear uptake by said strip and the length of the tear-wicked end portion of said strip is a substantially linear relationship.

5. A kit of claim 1, wherein said strip has noticeable marks thereon, wherein each of the marks indicates a volume of the tear fluid absorbed by the end portion up to that mark of said strip.

6. A kit of claim 1, wherein said analyte of interest is selected from the group consisting of: an electrolyte, a metallic element, a polypeptide hormone, a chronically administered medication, an acutely administered medication, a small molecule hormone, a marker of inflammation, a marker of allergy, a lipid, a protein, a marker of infection, and a metabolite.

7. A kit of claim 6, wherein said analyte of interest is lactoferrin.

8. A kit of claim 6, wherein said analyte of interest is glucose.

9. A kit of claim 1, wherein said testing agent composition comprises a receptor that is capable of binding reversibly said analyte of interest and has a detectable optical signal that changes in a concentration-dependent manner when the receptor is bound to said analyte, wherein said detectable optical signal results from one or more labels associated with the receptor.

10. A kit of claim 9, wherein said detectable optical change is selected from the group consisting of changes in fluorescent decay time, fluorescent intensity, fluorescent anisotropy, fluorescence polarization, a spectral shift of the emission spectrum, and a change in time-resolved anisotropy decay.

11. A kit of claim 9, wherein the testing agent composition comprises: (1) a fiuorescent energy donor and a fluorescent energy acceptor; or (2) a fluorescent energy donor and a non-fluorescent energy acceptor.

12. A kit of claim 9, wherein the testing agent composition is one or more solutions or is incorporated partially or fully in said strip.

13. A kit of claim 1, wherein the testing agent composition comprises a receptor having a first label associated therewith, a competitor having a second label associated therewith, wherein one of the first and second labels is a fluorescent energy donnor and the other one is a fluorescent or non-fluorescent energy acceptor said testing agent composition comprises a receptor and a competitor, wherein said receptor comprises a analyte/competitor binding site to which the analyte can be reversibly bound.

14. A kit of claim 13, wherein the testing agent composition is one or more solutions or is incorporated partially or fully in said strip.

* * * * *